(12) United States Patent　　　　(10) Patent No.:　US 12,685,848 B2
Kim　　　　　　　　　　　　　　　(45) Date of Patent:　　Jul. 21, 2026

(54) CHEST TUBE INSERTION DEVICE USING ENDOSCOPIC GUIDE

(71) Applicant: KOREA UNIVERSITY RESEARCH AND BUSINESS FOUNDATION, Seoul (KR)

(72) Inventor: Hyun Koo Kim, Seocho-gu (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 368 days.

(21) Appl. No.: 17/769,587

(22) PCT Filed: Oct. 21, 2020

(86) PCT No.: PCT/KR2020/014381
§ 371 (c)(1),
(2) Date: Apr. 15, 2022

(87) PCT Pub. No.: WO2021/080302
PCT Pub. Date: Apr. 29, 2021

(65) Prior Publication Data
US 2023/0117754 A1　　Apr. 20, 2023

(30) Foreign Application Priority Data

Oct. 23, 2019　(KR) ........................ 10-2019-0132333
Oct. 23, 2019　(KR) ........................ 10-2019-0132334

(51) Int. Cl.
*A61M 27/00*　　　(2006.01)
*A61B 1/00*　　　(2006.01)
(52) U.S. Cl.
CPC ......... *A61M 27/00* (2013.01); *A61B 1/00052* (2013.01); *A61B 1/00154* (2013.01);
(Continued)

(58) Field of Classification Search
CPC ..... A61B 1/313; A61B 1/00135; A61M 27/00
See application file for complete search history.

(56) References Cited

U.S. PATENT DOCUMENTS

2004/0153098 A1 *　8/2004　Chin ...................... A61B 90/11
　　　　　　　　　　　　　　　　　　　　　　600/374
2011/0023888 A1 *　2/2011　Vazales .............. A61B 1/00142
　　　　　　　　　　　　　　　　　　　　　　128/207.14
(Continued)

FOREIGN PATENT DOCUMENTS

JP　　2007-117114　　5/2007
JP　　2011-062459　　3/2011
(Continued)

OTHER PUBLICATIONS

International Search Report, International Patent Application No. PCT/KR2020/014381, mailed May 17, 2021, 2 pages.

*Primary Examiner* — Alexandra L Newton
(74) *Attorney, Agent, or Firm* — Casimir Jones, S. C.; Thomas J. Lyneis

(57)　　　　　　ABSTRACT

The present invention relates to a chest tube insertion device using an endoscopic guide, the device having a structure comprising: a tube insertion guide body which is made from a transparent or semitransparent synthetic resin material and which is introduced into the thoracic cavity of the human body while being flexibly bendable, an endoscopic tube disposed inside the tube insertion guide body; a chest tube formed as a structure for encompassing the outer side of the tube insertion guide body, so as to be spaced from the endoscopic tube; a guide holder for performing an endoscopic guide function and a tube insertion guide body fixing function when the tube insertion guide body is inserted into the thoracic cavity; and a handle part to which the guide holder is separably coupled.

3 Claims, 11 Drawing Sheets

(52) U.S. Cl.
CPC . *A61B 1/00195* (2013.01); *A61M 2205/3306* (2013.01); *A61M 2205/502* (2013.01); *A61M 2210/10* (2013.01)

(56) References Cited

U.S. PATENT DOCUMENTS

| | | | |
|---|---|---|---|
| 2015/0313634 A1* | 11/2015 | Gross | A61B 5/067 606/185 |
| 2015/0342699 A1 | 12/2015 | Cameron | |
| 2017/0209022 A1* | 7/2017 | Molnar | A61M 16/0465 |
| 2017/0360290 A1* | 12/2017 | Aho | A61B 1/00016 |
| 2019/0290890 A1 | 9/2019 | Dein | |

FOREIGN PATENT DOCUMENTS

| | | |
|---|---|---|
| JP | 4964452 | 6/2012 |
| KR | 10-2010-0030552 | 3/2010 |
| KR | 10-2016-0057933 | 5/2016 |

* cited by examiner

CHEST TUBE INSERTION DEVICE USING ENDOSCOPIC GUIDE

TECHNICAL FIELD

The following description relates to a real-time chest tube insertion guide device using an endoscopic guide, and more particularly, to a chest tube insertion guide technology using an endoscopic guide, which is capable of checking a structure in a patient's thoracic cavity and a disease state in the thoracic cavity during chest tube insertion and accurately identifying images of the inside of the thoracic cavity in real time by using an imaging device such as a monitor, a chest tube, and an endoscope separately accommodated in plurality of tube lines to perform safe chest tube insertion.

BACKGROUND ART

Chest tube insertion refers to a procedure of removing air, residual bodily fluid, blood, or the like by inserting a tube into a chest. The chest tube insertion is performed on injured patients who was subjected to pneumothorax treatment, pneumonectomy, or heart surgery, or patient with injured lung.

If air, bodily fluid, blood, and the like are accumulated in the chest of the human body, the organs in the human body may be compressed. Therefore, the chest tube insertion is performed to solve or prevent the above-mentioned problem or performed to observe hemorrhage that occurs after a period of time has elapsed even though the amount of residual blood is not large in the injured patient. Meanwhile, the chest tube insertion is required in various clinical situations. Unlike a drainage tube configured to be inserted into an abdomen or skin, the chest tube is sometimes used by being connected to a drainage container configured to prevent air from flowing reversely and into the thoracic cavity.

In general, the chest tubes have various thicknesses from 7 Fr to 32 Fr, and a chest tube having a large caliber is inserted when the amount of drainage is large or air leakage is severe. The chest tube with a large caliber is also inserted even after pulmonary surgery and cardiac surgery because the amount of drainage and air leakage is large.

The chest tube insertion is conducted after local anesthesia. After administering analgesics, the incision of 1 to 2 cm is made between the ribs into which the chest tube is intended to be inserted. Then, a surgical tool is used to form a hole in a pleura. In this case, the hole is formed above the ribs because the blood vessels and the nerves pass through a location below the ribs. Thereafter, the procedure is ended by inserting the chest tube, fixing the chest tube to the skin, and connecting the drainage container to the chest tube.

Meanwhile, during the chest tube insertion, the chest tube is not inserted into the chest but inserted into an abdominal cavity, which may damage the liver or spleen and cause hemorrhage. Rarely the chest tube damages the lung or heart, which may cause severe pneumothorax or hemorrhage. In addition, there is a problem in that the position of the chest tube is not appropriate, and the chest tube insertion is performed multiple times.

The above-mentioned chest tube used for the chest tube insertion in the related art performs a guide function. However, it is difficult to check structures and disease states in the patient's thoracic cavity on which the chest tube insertion needs to be performed. Further, it is impossible to identify a final position of the chest tube.

As described above, it is essential to position the chest tube at an appropriate position and prevent damage to organs in the thoracic and abdominal cavities to properly perform the chest tube insertion.

As a related document relevant to a technology related to a chest tube insertion device, there is Korean Patent Application Laid-Open No. 10-2010-0030552 (Mar. 18, 2010). The related document discloses a technology related to a chest tube insertion device capable of allowing a practitioner to quickly and accurately insert a chest tube into a thoracic cavity of a human body and conveniently perform chest tube insertion during a surgical procedure even though the practitioner is not a skilled surgeon.

(Patent Document 1) KR10-2010-0030552 A

DISCLOSURE OF THE INVENTION

Technical Goals

An aspect provides a real-time chest tube insertion device using an endoscopic imaging guide, which is capable of safely inserting a chest tube while checking various structures and disease states in a patient's thoracic cavity.

Another aspect provides a chest tube insertion device capable of being safely inserted into cut-out tissue while checking, in real time, through a monitor, images of the inside of the body acquired by an endoscope protected by a transparent lens in a state in which the endoscope and a chest tube are separately accommodated in a plurality of tube lines formed on a tube insertion guide body having a flexibly bendable structure.

Still another aspect provides a chest tube insertion device capable of safely inserting a chest tube into cut-out tissue while checking, through a monitor, images of the inside of the body acquired by an endoscope protected by a transparent lens, and then stably removing other components except for the chest tube by moving rearward a tube insertion guide body and the endoscope coupled in the chest tube.

Technical Solutions

According to an aspect, there is provided a chest tube insertion device using an endoscopic guide, the chest tube insertion device including: a tube insertion guide body made of a transparent or semi-transparent synthetic resin material and configured to be inserted into a thoracic cavity of a human body in a state in which the tube insertion guide body is flexibly bendable; an endoscope coupled to a first tube line formed in the tube insertion guide body; a chest tube coupled to a second tube line separated from the first tube line in the tube insertion guide body; a guide holder configured to perform an endoscopic guide function and a tube insertion guide body fixing function when the tube insertion guide body is inserted into the thoracic cavity; and a handle part to which the guide holder is separably coupled, in which the chest tube is safely inserted into the inside of the body as the chest tube is inserted through a tube insertion groove formed at a lateral side of the tube insertion guide body and then the tube insertion guide body is moved rearward.

According to another aspect, there is provided a chest tube insertion device using an endoscopic guide, the chest tube insertion device including: a tube insertion guide body made of a transparent or semi-transparent synthetic resin material and configured to be inserted into a thoracic cavity of a human body in a state in which the tube insertion guide body is flexibly bendable; an endoscope disposed on an endoscopic tube disposed in the tube insertion guide body; a chest tube structured to surround the tube insertion guide body and spaced apart from the endoscopic tube; a guide holder configured to perform an endoscopic guide function and a tube insertion guide body fixing function when the tube insertion guide body is inserted into the thoracic cavity; a handle part to which the guide holder is separably coupled; a transparent lens coupled to an opened front end of the tube insertion guide body; and a display part separably coupled to an upper end of the handle part, the display part being a portable smart device or a stationary monitor device, in which a practitioner holds, with hand, the chest tube inserted into thoracic cavity of the human body and moves rearward the tube insertion guide body coupled to the handle part in order to remove the endoscopic tube, the endoscope, and the tube insertion guide body and leave only the chest tube connected to the inside of the body.

The chest tube insertion device may further include a transparent lens coupled to an opened front end of the tube insertion guide body, and a front side of the transparent lens may include an inclined region.

A display part separably coupled to an upper end of the handle part may be a portable smart device or a stationary monitor device.

The transparent lens has a protruding region to which the endoscope is coupled, and an inclined region capable of entering or existing the chest tube.

Advantageous Effects

The real-time chest tube insertion device using an endoscopic guide according to the present invention described above may check, in real time, a structure in a patient's thoracic cavity and a disease state in the thoracic cavity during the chest tube insertion. Further, the real-time chest tube insertion device may accurately identify images of the inside of the thoracic cavity by using an imaging device such as an endoscope and a monitor for safe chest tube insertion.

According to the chest tube insertion device using an endoscopic guide according to the present invention described above, it is possible to safely insert the chest tube into cut-out tissue while checking, through the monitor, the images of the inside of the body acquired by the endoscope protected by the transparent lens and the endoscopic tube. Thereafter, it is possible to stably remove other components except for the chest tube by integrally moving rearward the tube insertion guide body and the endoscope coupled in the chest tube.

According to the present invention, the tube insertion guide body and the endoscope are positioned inside the chest tube, which makes it possible to minimize a diameter of the device configured to be inserted into the human body. Further, according to the present invention, since the endoscope is protected by the internal structure of the tube insertion guide body and the transparent lens, the endoscope may be used multiple times or permanently.

According to the present invention, it is possible to accurately identify the images of the inside of the thoracic cavity in real time in order to solve the problem of hemorrhage and pneumothorax that occurs when chest tube insertion in the related art is performed.

BEST MODE FOR CARRYING OUT THE INVENTION

Figure 1:
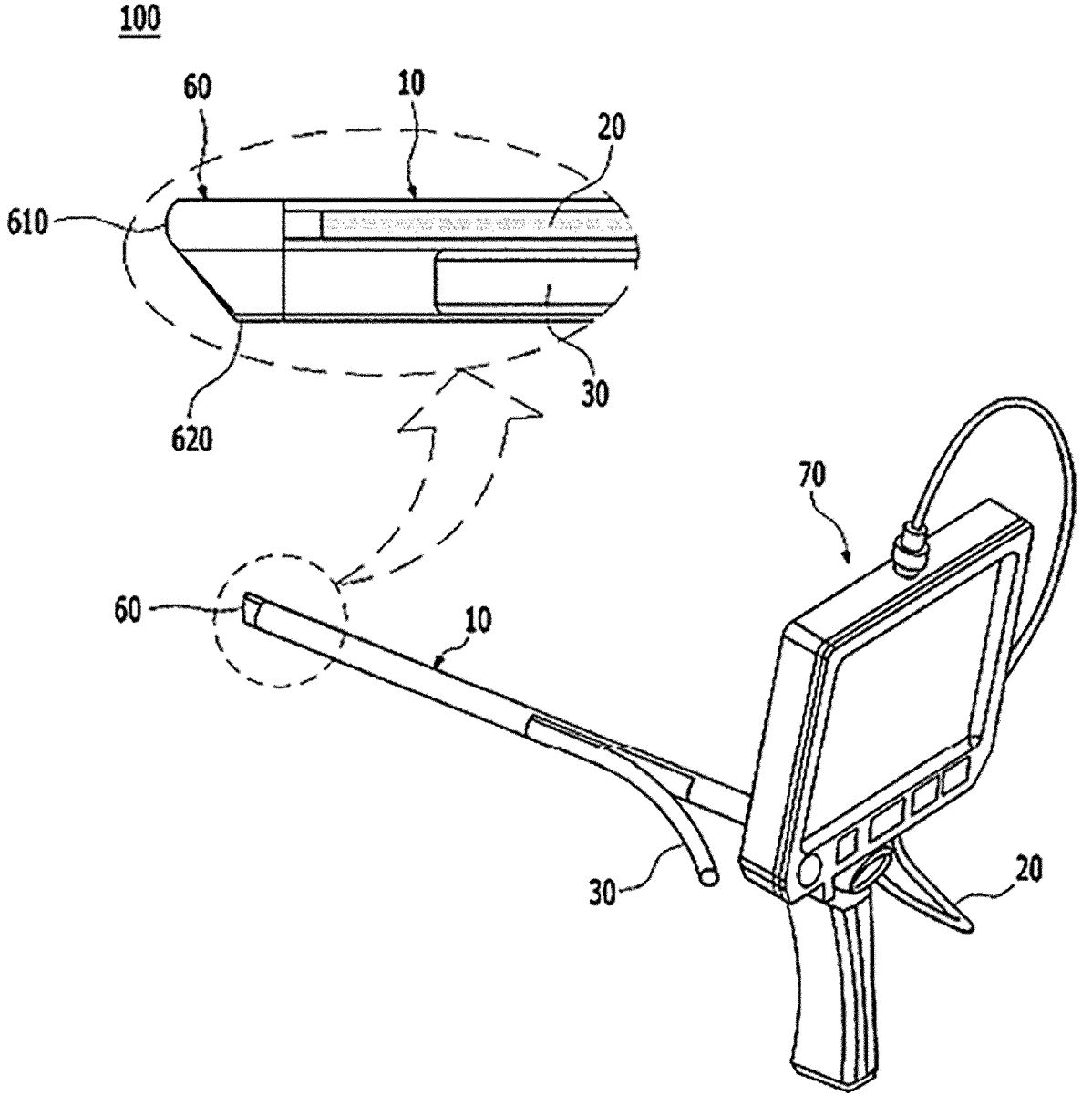
FIG. 1 is a perspective view illustrating an overall concept of a chest tube insertion device using an endoscopic guide according to an embodiment of the present invention.

Hereinafter, embodiments of the present invention will be described in more detail with reference to the accompanying drawings. However, the present invention is not limited to the exemplary embodiment disclosed herein but will be implemented in various forms. The exemplary embodiment of the present invention is provided so that the present invention is completely disclosed, and a person with ordinary skill in the art can fully understand the scope of the present invention. In the drawings, the same reference numerals refer to the same elements.

In giving reference numerals to constituent elements of the respective drawings, it should be noted that the same constituent elements will be designated by the same reference numerals, if possible, even though the constituent elements are illustrated in different drawings. In addition, in the description of the present invention, the specific descriptions of publicly known related configurations or functions will be omitted when it is determined that the specific descriptions may obscure the subject matter of the present invention.

Hereinafter, a chest tube insertion guide device using an endoscopic guide according to an embodiment of the present invention will be described with reference to FIGS. 1 to 3.

A chest tube insertion device 100 using an endoscopic guide according to the present invention includes: a tube insertion guide body 10 made of a transparent or semi-transparent synthetic resin material and configured to be inserted into a thoracic cavity of a human body in a state in which the tube insertion guide body 10 is flexibly bendable; an endoscope 20 coupled to a first tube line formed in the tube insertion guide body 10; a chest tube 30 coupled to a second tube line formed separately from the first tube line in the tube insertion guide body; a guide holder 40 configured to perform an endoscopic guide function and a tube insertion guide body fixing function when the tube insertion guide body is inserted into the thoracic cavity; a handle part 50 to which the guide holder is separably coupled; a transparent lens 60 coupled to an opened front end of the tube insertion guide body; and a display part 70 separably coupled to an upper end of the handle part, the display part 70 being a portable smart device or a stationary monitor device.

The display part 70 further includes a control unit detachably disposed on the handle part and connected to the endoscope 20. The control unit and the display part are connected in a wireless or wired manner.

The tube insertion guide body 10 has a structure in which the first tube line 110, in which the endoscope 20 is disposed, and the second tube line 120, in which the chest tube 30 is disposed, are disposed in parallel in a longitudinal direction but do not communicate with each other. That is, the endoscope 20 connected to the display part 70 is separably inserted into the first tube line 110, and the chest tube 30 is separably inserted into the second tube line 120 through a tube insertion groove 122 formed at a lateral side of the second tube line 120.

A cross-section of the tube insertion guide body 10 has a roly-poly shape having a width that gradually increases from an upper side to a lower side thereof. A diameter of the first tube line 110 disposed at the upper side may be maintained to be 11 Fr, and a diameter of the second tube line 120 disposed at the lower side may be maintained to be 24 Fr. In this case, a length of the tube insertion guide body 10 based on an upward/downward direction may be 15.8 mm, and a width of the tube insertion guide body 10 based on a leftward/rightward direction may be 10.5 mm.

The endoscope 20 is disposed so that a practitioner may recognize, through the display part 70, a state in which the tube insertion guide body 10 is inserted into the human body through a pleura. For example, the endoscope 20 is kept separably inserted into the first tube line that defines the upper side of the tube insertion guide body 10 and is formed in the longitudinal direction of the tube insertion guide body 10. The endoscope 20 may be an attachable/detachable device and continually used by being disinfected. The tube insertion guide body 10 may be used as a disposable product. The endoscope 20 includes an image capturing unit and a light-emitting unit.

Only the chest tube 30 is inserted into the inside of the body by a process of inserting the chest tube 30 through the tube insertion groove 122 formed at the lateral side of the tube insertion guide body 10 and then moving rearward the tube insertion guide body 10 coupled to the handle part 50.

The guide holder 40 may have a structure in which an end of the tube insertion guide body 10 is separably inserted into the guide holder 40 and the endoscope 20 is coupled to the guide holder 40 so as to operate in conjunction with the guide holder 40. The guide holder 40 may have a shape having a diameter that gradually decreases from a front side, to which the tube insertion guide body 10 is coupled, to a rear side thereof.

The handle part 50 may include a grip portion 510 configured to be grasped by the practitioner, and a guide portion disposed in an inclined state on an upper end of the grip portion. The guide portion has a shape in which an upper end of the guide portion is gradually inclined downward to conform to the shape of the guide holder 40 having the diameter that gradually decreases from the front side to the rear side thereof.

The display part 70 shows the practitioner images received from the endoscope 20, and the practitioner easily recognizes a structure of the inside of the patient body through the display part 70. The display part 70 may enlarge images having passed through a lens of the endoscope 20 and output the images. The display part 70 may produce static images and record videos. The display part 70 may have an image storage memory and an interface to be connected to an external device.

As the display part 70, based on the user's convenience, a portable electronic device such as a smartphone may be adopted or monitoring may be performed through a large-scale screen implemented by a stationary monitor device. Meanwhile, the light-emitting unit may be disposed at one side end of the tube insertion guide body 10 and use a light source such as an LED. The light-emitting unit may use at least any one of visible rays, infrared rays, and ultraviolet rays.

The transparent lens 60 is coupled to the front end of the tube insertion guide body 10. A front region of the transparent lens is in an inclined state. The transparent lens 60 has a protruding region connected to the first tube line to which the endoscope 20 is coupled, and an inclined region connected to the second tube line into which the chest tube 30 is inserted. The transparent lens 60 performs a function of ensuring a visual field of an endoscope camera when the tube insertion guide body 10 is inserted into the human body.

Hereinafter, a process of using the chest tube insertion guide device using an endoscopic guide will be described with reference back to FIGS. 1 to 3.

The tube insertion guide body 10 is deformed to a desired shape before the tube insertion guide body 10 is inserted into the inside of the body. As described above, the tube insertion guide body 10 is inserted into the thoracic cavity of the human body in the state in which the tube insertion guide body 10 is kept flexibly bent, such that the tube insertion guide body 10 may be safely inserted into the chest.

After the tube insertion guide body 10 is safely inserted into the human body through the endoscope camera and the transparent lens 60 and disposed at a proper position at which bodily fluid or blood remains in lung tissue, the bodily fluid or blood is discharged to the outside of the body through the tube insertion groove 122 formed at the lateral side of the tube insertion guide body 10 after the chest tube 30 is inserted.

Meanwhile, according to the present invention, the practitioner may check, in real time, a state of the inside of the body through the endoscope 20 disposed in the first tube line separated from the second tube line in the tube insertion guide body 10 while the fluid is discharged through the chest tube 30 disposed in the second tube line formed in the tube insertion guide body 10.

After the above-mentioned process, the practitioner holds the chest tube 30 with his/her hand and moves rearward the tube insertion guide body 10 coupled to the handle part 50, thereby leaving only the chest tube 30 connected to the inside of the body.

Hereinafter, a chest tube insertion device 100' using an endoscopic guide according to another embodiment of the present invention will be described with reference to FIGS. 4 to 6.

The chest tube insertion device 100' using an endoscopic guide includes: a tube insertion guide body 10 configured to be inserted into a thoracic cavity of a human body in a state in which the tube insertion guide body 10 is flexibly bendable; an endoscope 20 disposed in an endoscopic tube 150 disposed in the tube insertion guide body 10; a chest tube 30 disposed outside the tube insertion guide body 10, structured to surround the tube insertion guide body 10, and spaced apart from the endoscopic tube 150; a guide holder 40 configured to perform an endoscopic guide function and a tube insertion guide body fixing function when the tube insertion guide body 10 is inserted into the thoracic cavity; a handle part 50 to which the guide holder is separably coupled; a transparent lens 60 coupled to an opened front end of the tube insertion guide body; and a display part 70 separably coupled to an upper end of the handle part, the display part 70 being a portable smart device or a stationary monitor device.

The tube insertion guide body 10 is provided in the form of a hollow tube made of a metallic material. The tube insertion guide body 10 is inserted into the thoracic cavity of the human body is flexibly bendable. Based on the tube insertion guide body 10, the endoscopic tube 150 is disposed inside the tube insertion guide body 10, and the chest tube 30 is disposed outside the tube insertion guide body 10. In the above-mentioned state, the transparent lens 60 is coupled to the front side of the tube insertion guide body 10, and the guide holder 40 is coupled to the rear side of the tube insertion guide body 10.

Meanwhile, a spiral guide groove is formed in the longitudinal direction in an outer peripheral surface of the tube insertion guide body 10. The guide may increase mobility between the tube insertion guide body 10 and the chest tube 30.

In the state in which the endoscopic tube 150, the endoscope 20, and the tube insertion guide body 10 are disposed in the chest tube 30, the transparent lens 60 is coupled to the front ends of the endoscopic tube 150 and the tube insertion guide body 10.

An inclined entry portion 310 is tapered at an outer side of the front end of the chest tube 30. That is, the entry portion is inclined so that the chest tube 30 is smoothly inserted into or separated from the thoracic cavity.

The endoscope 20 is disposed so that a practitioner may recognize, through the display part 70, a state in which the tube insertion guide body 10 is inserted into the human body through a pleura. For example, the endoscope 20 is kept separably inserted into the tube line formed in the longitudinal direction of the tube insertion guide body 10. The endoscope 20 may be an attachable/detachable device and continually used by being disinfected. The tube insertion guide body 10 may be used as a disposable product. The endoscope 20 includes an image capturing unit and a light-emitting unit.

Figure 2:
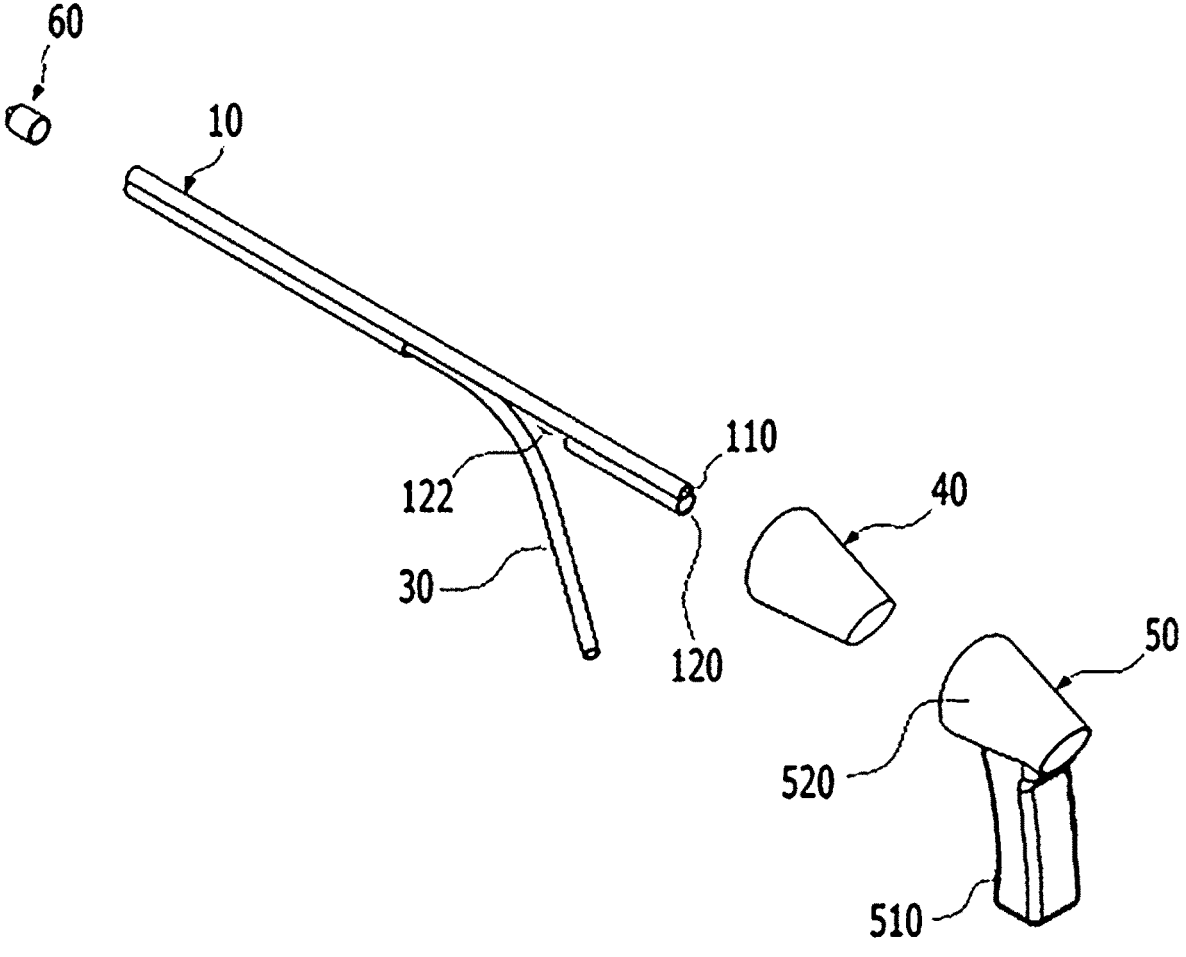
FIG. 2 is an exploded perspective view of the chest tube insertion device in FIG. 1.
Figure 3:
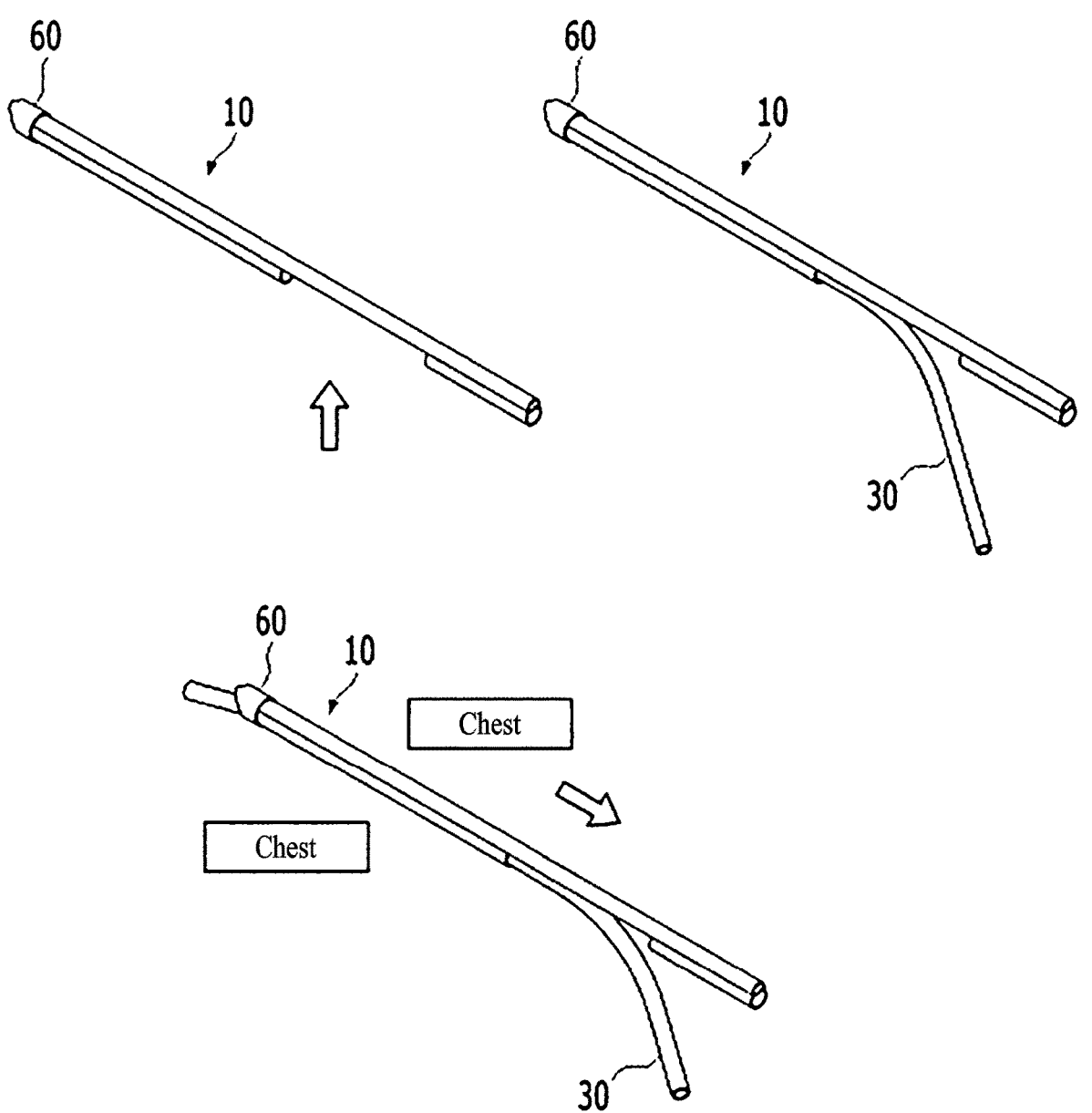
FIG. 3 is a view illustrating a process in which a chest tube is inserted through a tube insertion guide body of the chest tube insertion device in FIG. 1.
Figure 4:
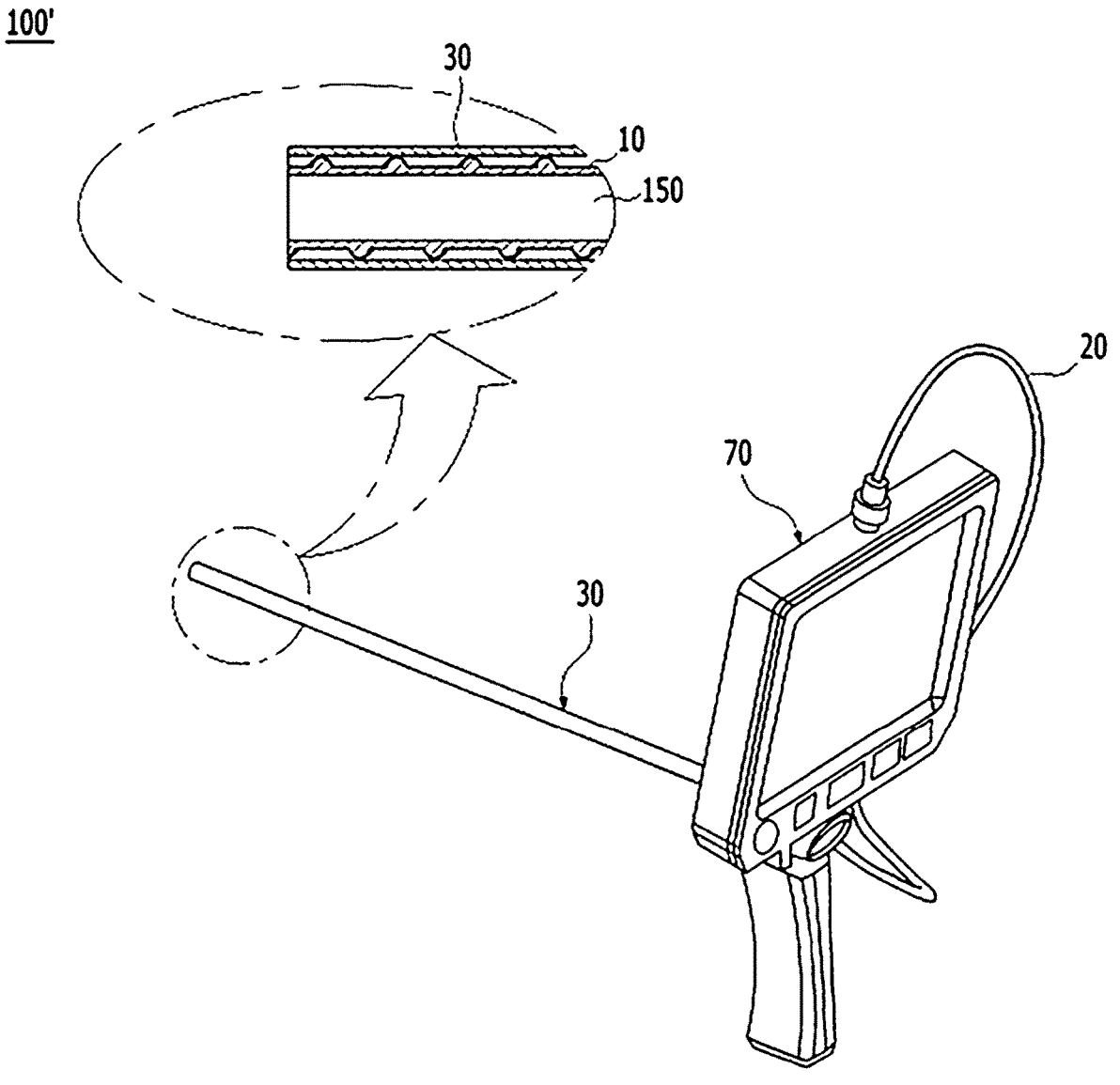
FIG. 4 is a perspective view illustrating an overall concept of a chest tube insertion device using an endoscopic guide according to another embodiment of the present invention.
Figure 5:
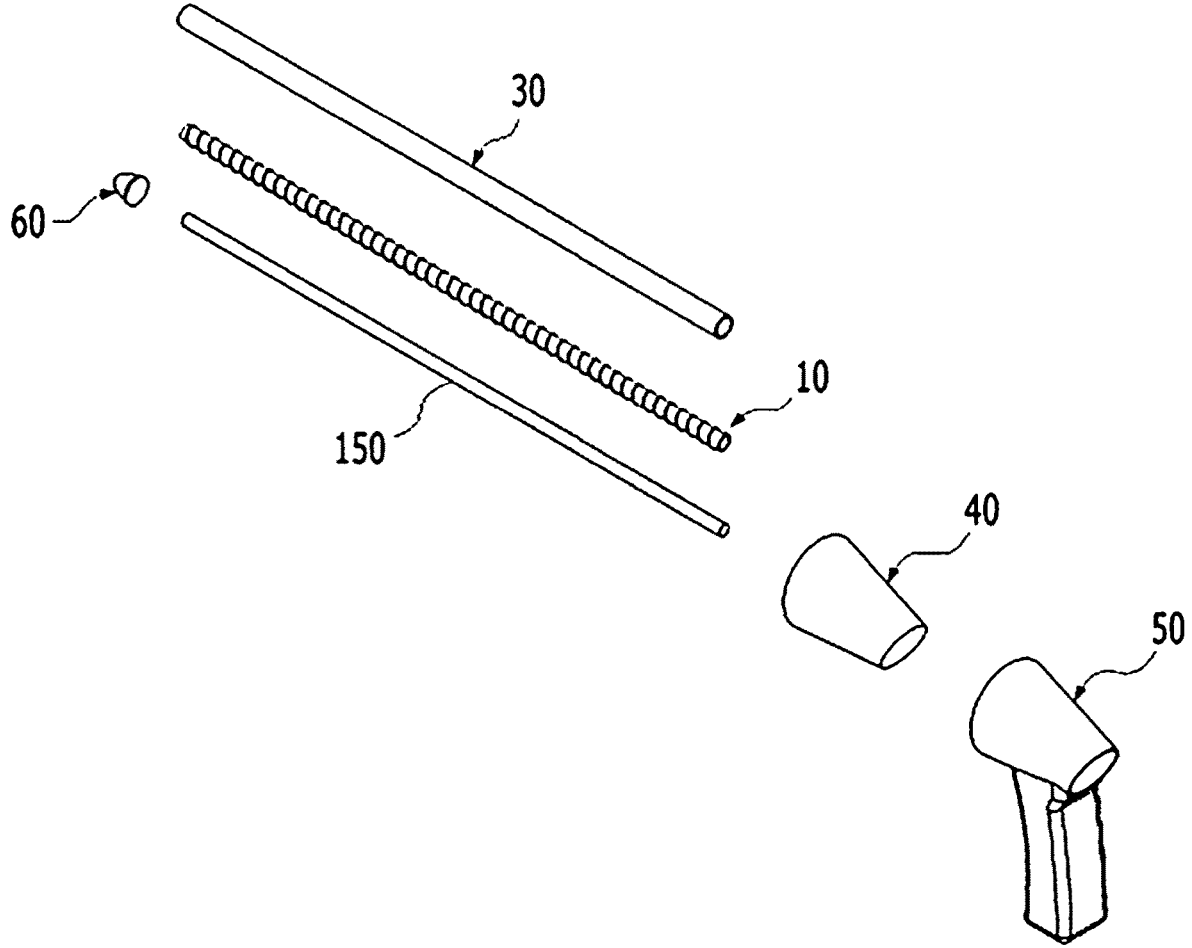
FIG. 5 is an exploded perspective view of the chest tube insertion device in FIG. 4.
Figure 6:
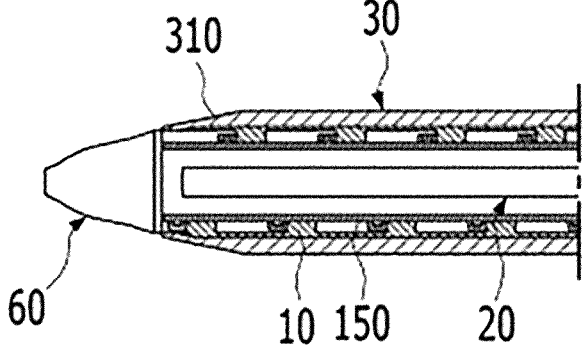
FIG. 6 is a view illustrating a cross-section taken in a longitudinal direction of the chest tube insertion device in FIG. 4 and illustrating a process of inserting a chest tube into the inside of the body and then integrally removing a tube insertion guide body and endoscope by moving rearward the endoscope and the tube insertion guide body coupled to an inner portion of the chest tube.
Figure 6:
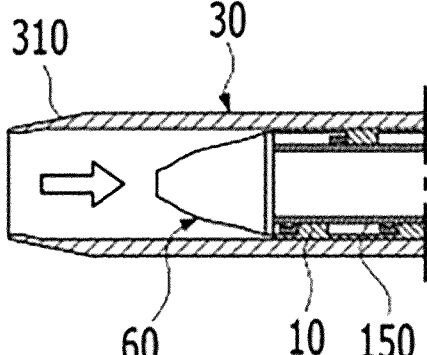

The endoscope 20, the guide holder 40, the handle part 50, the transparent lens 60, and the display part 70, which are illustrated in FIGS. 4 to 6, are substantially identical to those illustrated in FIGS. 1 to 3 except for the descriptions illustrated in FIGS. 4 to 6.

Hereinafter, a process of using the chest tube insertion guide device using an endoscopic guide will be described with reference back to FIGS. 4 to 6.

The tube insertion guide body 10 is deformed to a desired shape before the chest tube 30 is inserted into the inside of the body. As described above, the tube insertion guide body 10 is inserted into the thoracic cavity of the human body in the state in which the tube insertion guide body 10 is kept flexibly bent, such that the tube insertion guide body 10 may be safely inserted into the chest. In this case, the chest tube 30 is deformed to the same shape as the tube insertion guide body 10 movably disposed in the chest tube 30 as the tube insertion guide body 10 is deformed in shape. That is, the flexible tube insertion guide body 10 made of a metallic material may be deformed when an external force is applied thereto, and the deformed shape of the tube insertion guide body 10 may be maintained.

After the tube insertion guide body 10 is safely inserted into the human body through the endoscope camera and the transparent lens 60 and disposed at a proper position at which bodily fluid or blood remains in lung tissue, the practitioner holds the chest tube 30 with his/her hand and moves rearward the tube insertion guide body 10 coupled to the handle part 50, thereby leaving only the chest tube 30 connected to the inside of the body.

Specifically, the practitioner holds the chest tube 30 with his/her hand and moves rearward the tube insertion guide body 10 coupled to the handle part 50, thereby removing the endoscopic tube 150, the endoscope 20, and the tube insertion guide body 10 and leaving only the chest tube 30 connected to the inside of the body. During the above-mentioned process, the transparent lens 60 coupled to the front ends of the endoscopic tube 150 and the tube insertion guide body 10 is also removed from the inside of the body. As a result, the bodily fluid or blood is discharged to the outside of the body in the state in which one side of the chest tube 30 is inserted into the inside of the body.

FIGS. 7 to 11 are views illustrating embodiments according to the present invention.

Figure 7:
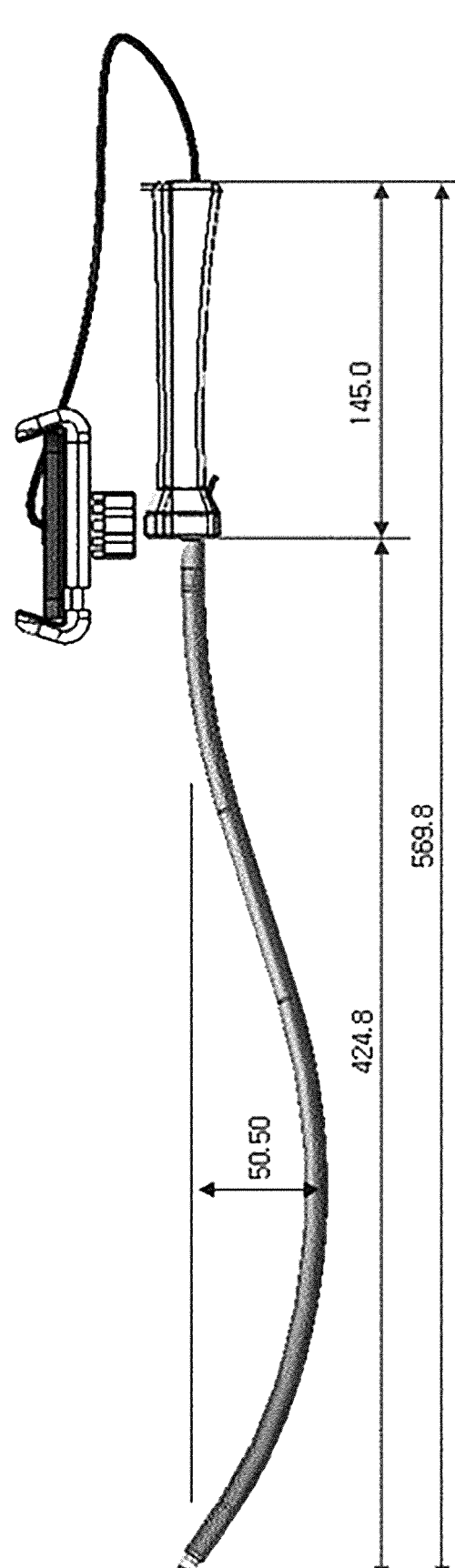
FIGS. 7 to 11 are views illustrating embodiments according to the present invention.
Figure 8:
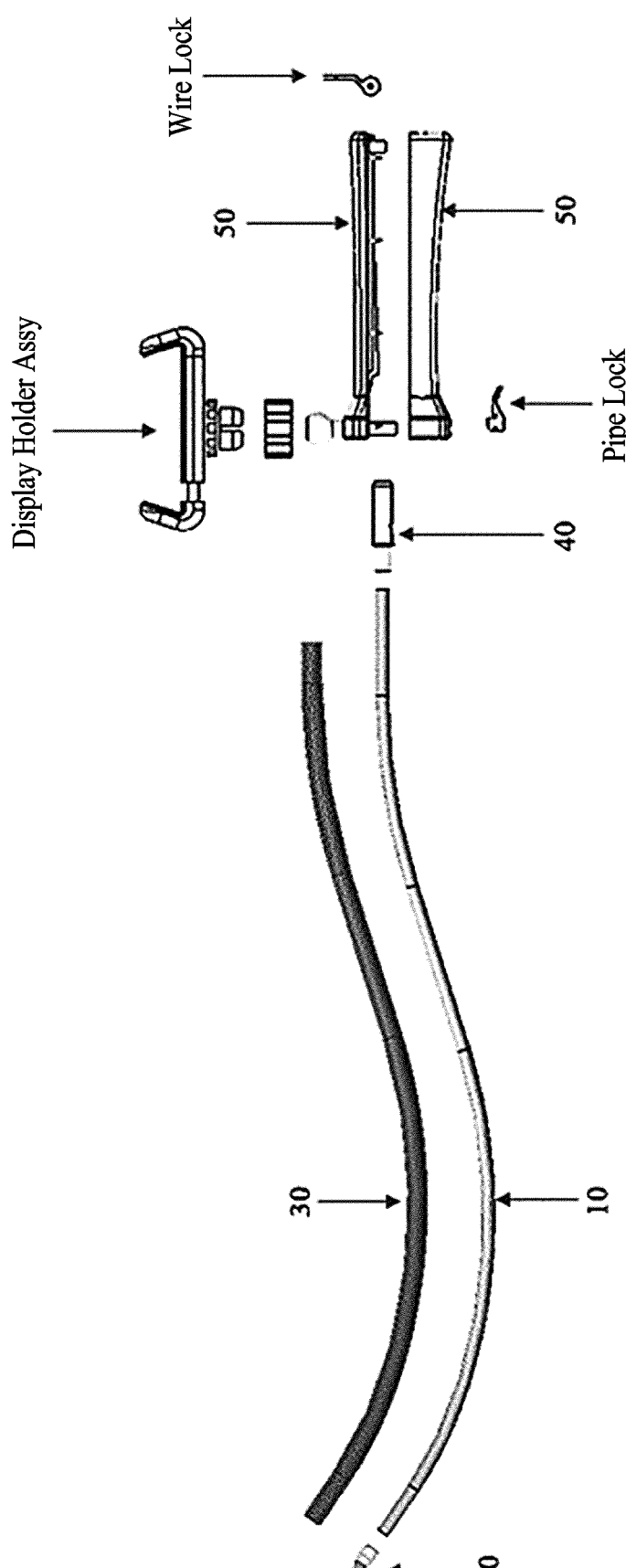
Figure 9:
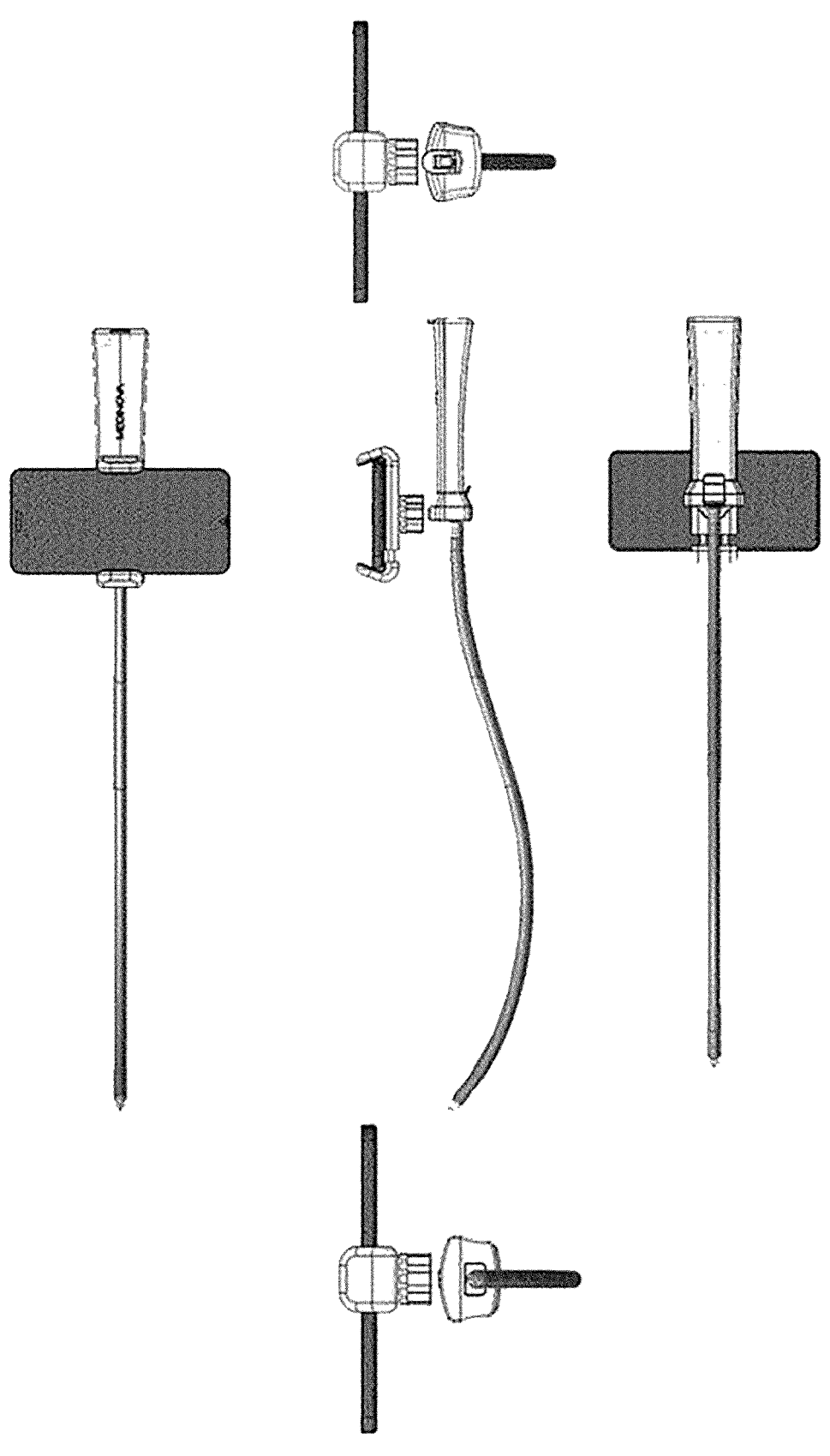
Figure 10:
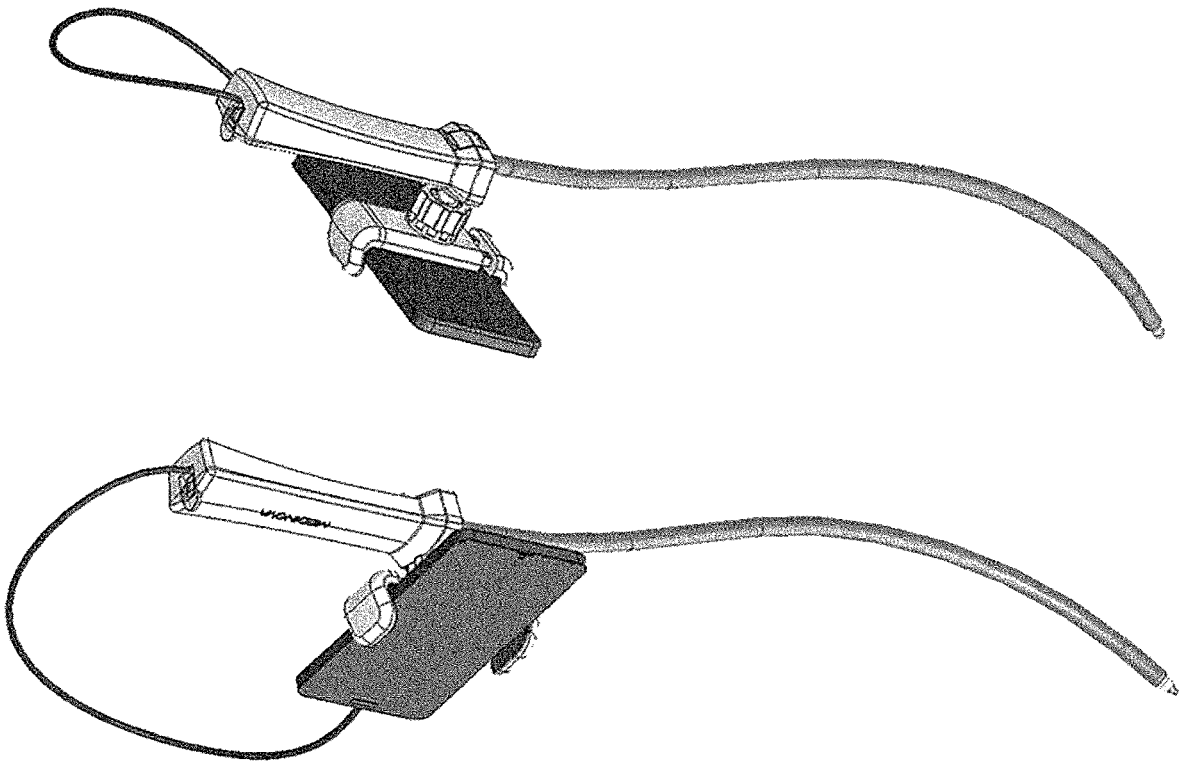
Figure 11:
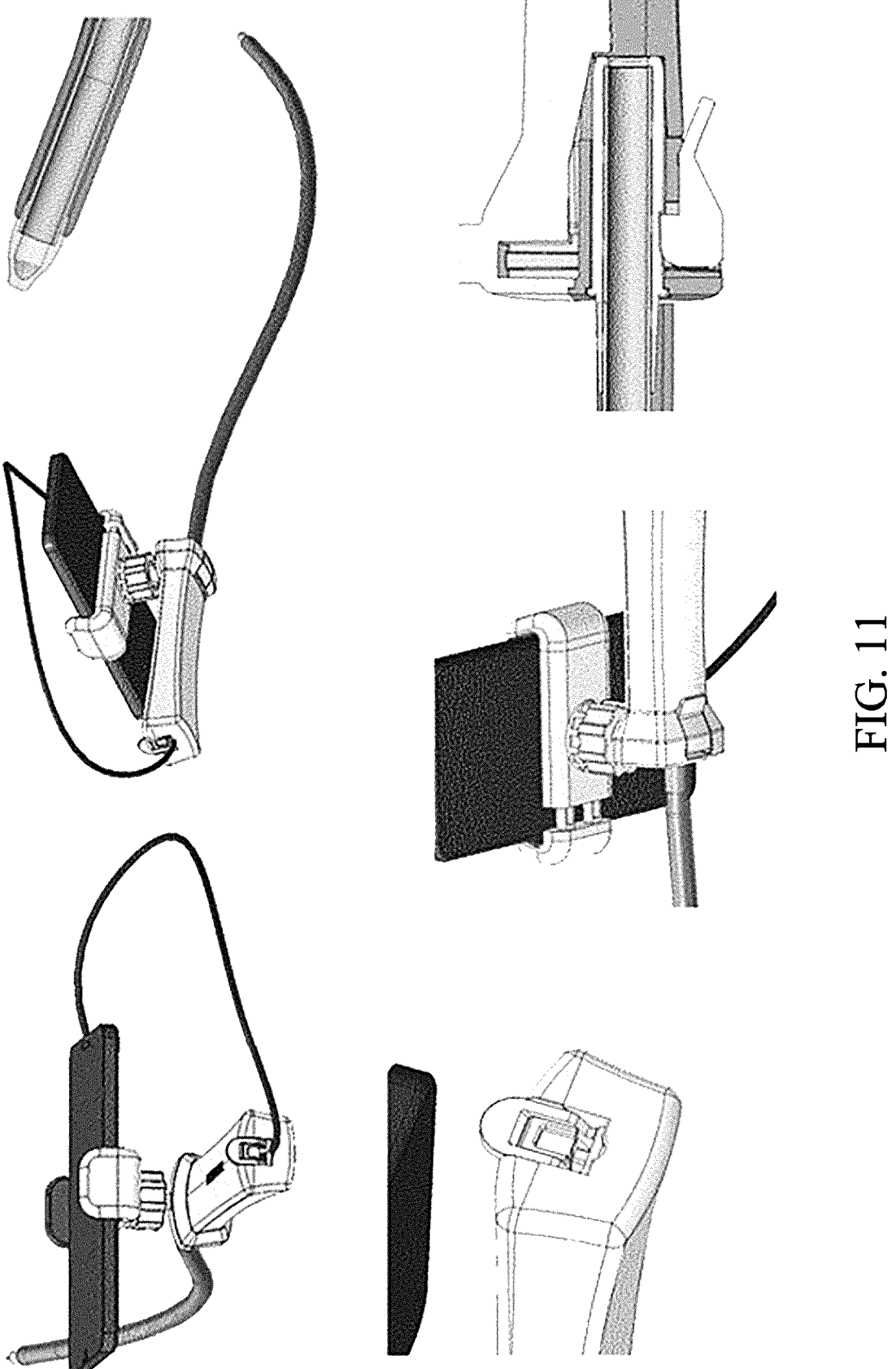

FIG. 7 illustrates dimensions of the chest tube insertion guide device using an endoscopic guide according to the embodiment, FIG. 8 illustrates disassembled states of the tube insertion guide body 10, the chest tube 30, the guide holder 40, the handle part 50, the transparent lens 60, and the display holder of the chest tube insertion guide device using an endoscopic guide according to the embodiment, and FIGS. 9 to 11 are 3D views illustrating an assembled state of the chest tube insertion guide device using an endoscopic guide according to the embodiment.

Hereinafter, various embodiments of the present invention will be described.

(1) A chest tube insertion device using an endoscopic guide, the chest tube insertion device including: a tube insertion guide body made of a transparent or semi-transparent synthetic resin material and configured to be inserted into a thoracic cavity of a human body in a state in which the tube insertion guide body is flexibly bendable; an endoscope coupled to a first tube line formed in the tube insertion guide body; a chest tube coupled to a second tube line separated from the first tube line in the tube insertion guide body; a guide holder configured to perform an endoscopic guide function and a tube insertion guide body fixing function when the tube insertion guide body is inserted into the thoracic cavity; and a handle part to which the guide holder is separably coupled, in which the chest tube is safely inserted into the inside of the body as the chest tube is inserted through a tube insertion groove formed at a lateral side of the tube insertion guide body and then the tube insertion guide body is moved rearward.

(2) The chest tube insertion device further including a transparent lens coupled to an opened front end of the tube insertion guide body, and a front side of the transparent lens includes an inclined region.

(3) In the chest tube insertion device, a display part separably coupled to an upper end of the handle part is a portable smart device or a stationary monitor device.

(4) In the chest tube insertion device, the transparent lens has a protruding region to which the endoscope is coupled, and an inclined region capable of entering or existing the chest tube.

(5) A chest tube insertion device using an endoscopic guide, the chest tube insertion device including: a tube insertion guide body made of a transparent or semi-transparent synthetic resin material and configured to be inserted into a thoracic cavity of a human body in a state in which the tube insertion guide body is flexibly bendable; an endoscope disposed in an endoscopic tube disposed in the tube insertion guide body; a chest tube structured to surround an outer side of the tube insertion guide body and spaced apart from the endoscopic tube; a guide holder configured to perform an endoscopic guide function and a tube insertion guide body fixing function when the tube insertion guide body is inserted into the thoracic cavity; a handle part to which the guide holder is separably coupled; a transparent lens coupled to an opened front end of the tube insertion guide body; and a display part separably coupled to an upper end of the handle part, the display part being a portable smart device or a stationary monitor device, in which a practitioner holds, with hand, the chest tube inserted into thoracic cavity of the human body and moves rearward the tube insertion guide body coupled to the handle part in order to remove the endoscopic tube, the endoscope, and the tube insertion guide body and leave only the chest tube connected to the inside of the body.

The chest tube insertion guide device using an image guide according to the present invention described above may check a structure in a patient's thoracic cavity and a disease state in the thoracic cavity during the chest tube insertion. Further, the chest tube insertion guide device may accurately identify images of the inside of the thoracic cavity by using an imaging device such as an endoscope and a monitor for safe chest tube insertion.

The chest tube insertion guide device using an image guide according to the present invention described above may check, in real time, a structure in a patient's thoracic cavity and a disease state in the thoracic cavity during the chest tube insertion. Further, the chest tube insertion guide device may accurately identify images of the inside of the thoracic cavity by using an imaging device such as an endoscope and a monitor to perform safe chest tube insertion.

The above description is simply given for illustratively describing the technical spirit of the present invention, and those skilled in the art to which the present invention pertains will appreciate that various changes and modifications are possible without departing from the essential characteristic of the present invention. Therefore, the exemplary embodiments disclosed in the present invention are provided for illustrative purposes only but not intended to limit the technical spirit of the present invention. The scope of the technical spirit of the present invention is not limited thereby. The protective scope of the present invention should be construed based on the following claims, and all the technical spirit in the equivalent scope thereto should be construed as falling within the scope of the present invention.

The invention claimed is:

1. A chest tube insertion device using an endoscopic guide, the chest tube insertion device comprising:
a tube insertion guide body made of a transparent or semi-transparent synthetic resin material and configured to be inserted into a thoracic cavity of a human body in a state in which the tube insertion guide body is flexibly bendable;
an endoscopic tube disposed within a first tube line formed in the tube insertion guide body;
an endoscope disposed in the endoscopic tube;
a chest tube coupled to a second tube line formed in the tube insertion guide body and separated from the first tube line in a longitudinal direction;
a guide holder configured to insert the endoscope through the tube insertion guide body positioned into the thoracic cavity and fix the inserted endoscope;
a handle part to which the guide holder is coupled;
a transparent lens coupled to an opened front end of the tube insertion guide body, wherein the transparent lens has a protruding region connected to the first tube line to which the endoscope is coupled, and an inclined region connected to the second tube line into which the chest tube is inserted; and wherein a practitioner holds, with hand, the chest tube inserted into the thoracic cavity of the human body and moves rearward the tube insertion guide body coupled to the handle part in order to remove the endoscopic tube, the endoscope, the tube insertion guide body and leave only the chest tube connected to the inside of the body, wherein the chest tube is inserted through a tube insertion groove formed at a lateral side of the second tube line.

2. The chest tube insertion device of claim 1, wherein a front side of the transparent lens comprises an inclined region, and the endoscope is removed together with the endoscopic tube and the tube insertion guide body when the endoscopic tube and the tube insertion guide body are removed.

3. The chest tube insertion device of claim 1, comprising:
a display part separably coupled to an upper end of the handle part, the display part being a portable smart device or a stationary monitor device.

* * * * *